United States Patent [19]

Gatturna

[11] 4,223,969
[45] Sep. 23, 1980

[54] QUICK CONNECT-DISCONNECT ELECTROFLUIDIC JUNCTION ASSEMBLY

[75] Inventor: Roland Gatturna, Walpole, Mass.

[73] Assignee: Codman & Shurtleff, Inc., Randolph, Mass.

[21] Appl. No.: 31,719

[22] Filed: Apr. 20, 1979

[51] Int. Cl.³ .............................................. H01R 4/64
[52] U.S. Cl. .................................... 339/15; 339/16 R;
339/183
[58] Field of Search ...................... 339/15, 16 R, 16 C,
339/183

[56] References Cited

U.S. PATENT DOCUMENTS

| | | | |
|---|---|---|---|
| 2,703,393 | 3/1955 | Bird | 339/183 |
| 3,649,948 | 3/1972 | Porter | 339/183 X |

*Primary Examiner*—Roy Lake
*Assistant Examiner*—DeWalden W. Jones

[57] ABSTRACT

A quick connect-disconnect electrofluidic junction assembly for simultaneously transferring fluid and electrical energy from respective sources of supply. The assembly includes a female terminal with an internal receptacle one end of which is open and surrounded by a peripheral wall. An electrical contact is positioned inside the housing and spaced apart from the open end. A fluid passage extends through the housing and communicates with the receptacle. A male terminal includes a hollow connector body which is adapted to be push-fit into the receptacle through its open end, with an electrical contact on its forward end adapted to mate with the electrical contact in the housing. A sealing element is located around the periphery of the body for providing a fluid-tight seal between the body and the interior wall of the housing when inserted therein. A fluid channel extends through the body between its forward end and the peripheral sealing element, so that fluid may be received from the receptacle, and then pass on through the body along with electrical leads whereby both an electrical and fluid connection can be made to the assembly.

10 Claims, 8 Drawing Figures

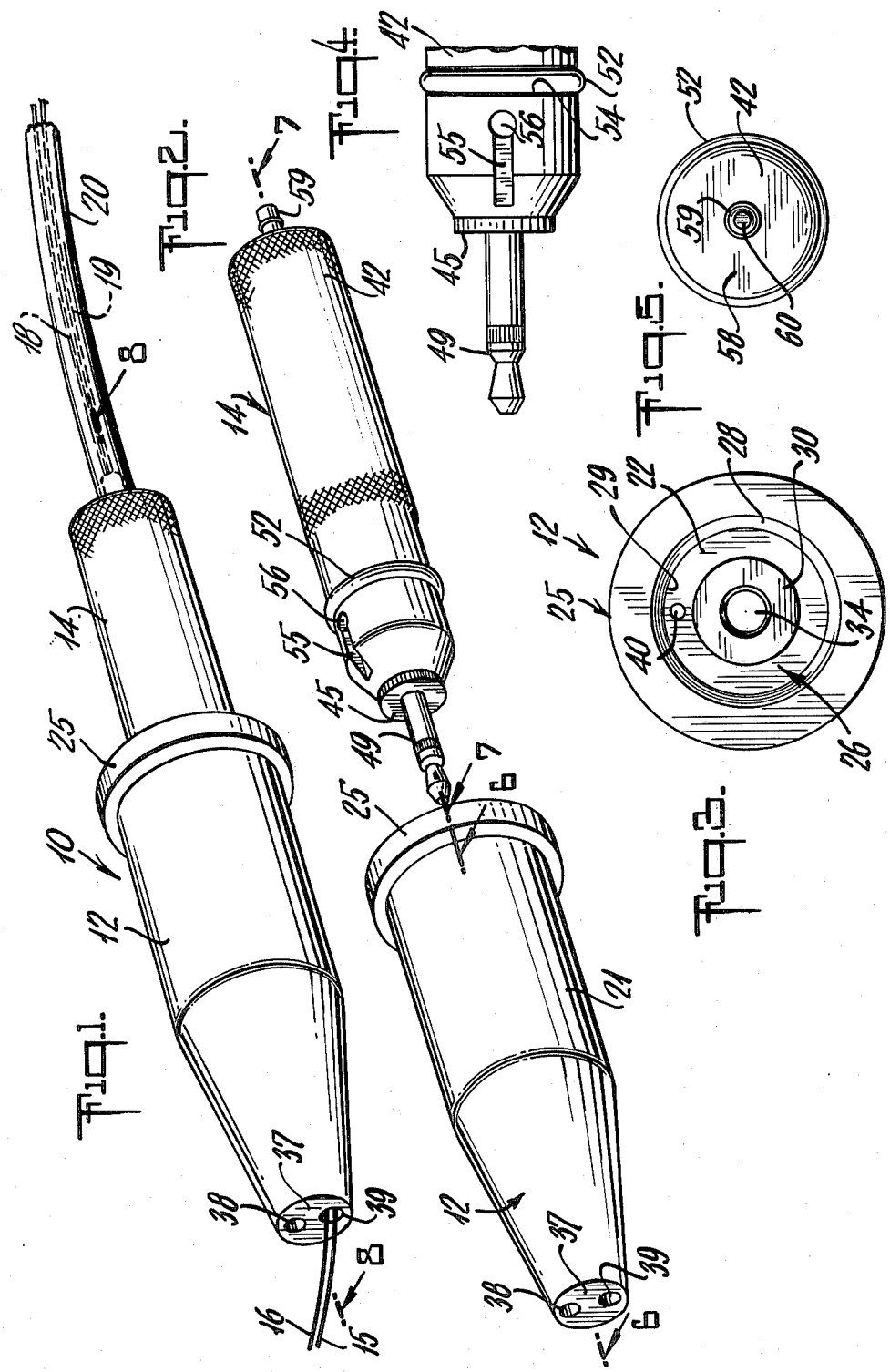

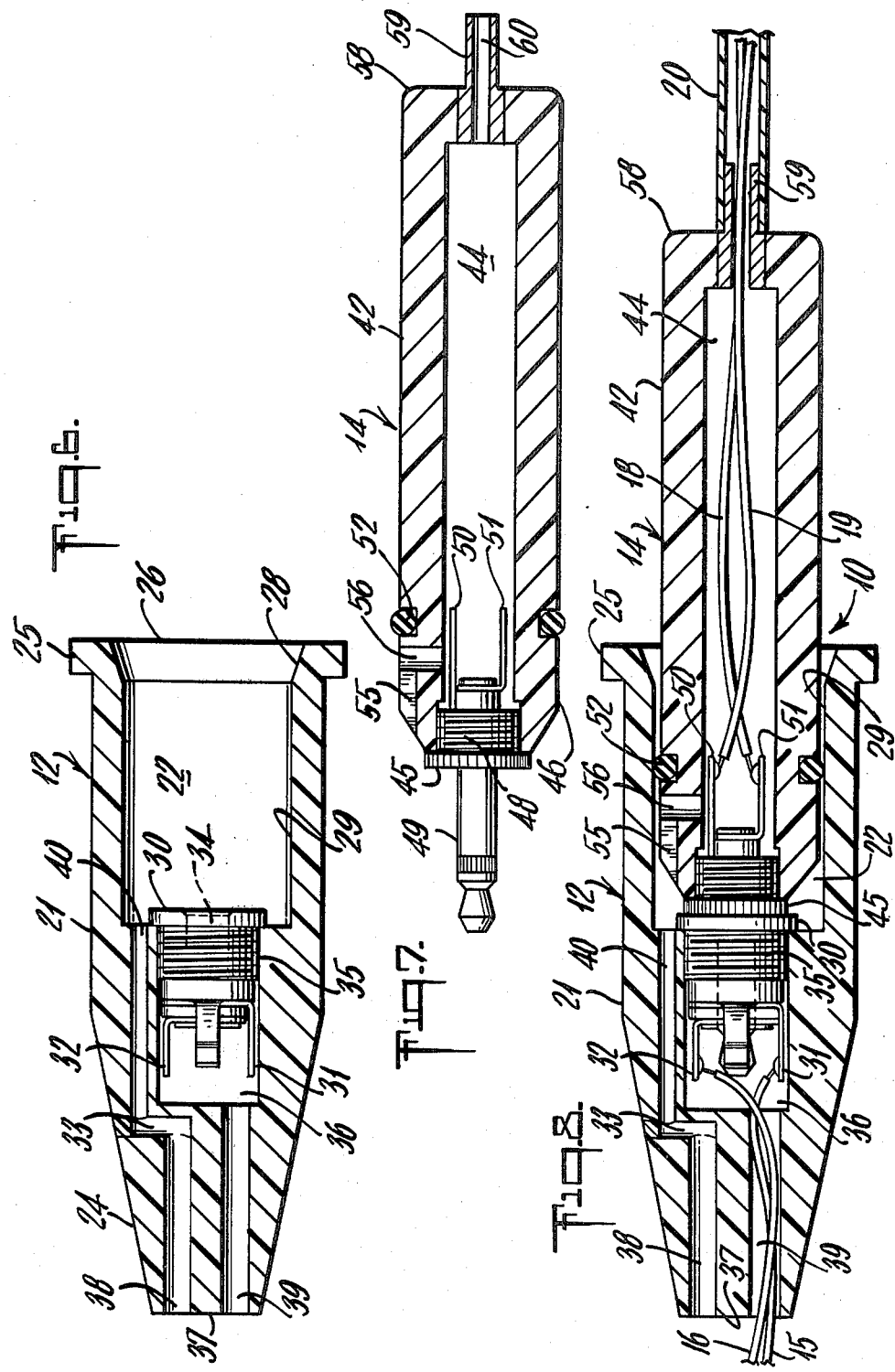

QUICK CONNECT-DISCONNECT ELECTROFLUIDIC JUNCTION ASSEMBLY

BACKGROUND OF THE INVENTION

The present invention relates to an assembly for simultaneously providing an electrical and fluidic junction, and more particularly concerns an electrofluidic junction assembly adapted for quick connect-disconnect purposes and used in situations where fluid and electrical energy are to be transferred simultaneously from respective sources of supply.

Although there are many other instances where the transfer of electrical and fluid energy are to be transferred simultaneously, one particular situation involves the monitoring of intracranial pressure inside a patient's skull. A device called a "Numoto" switch is employed in this task of monitoring intracranial pressure, and utilizes both electrical and fluidic, particularly pneumatic, energy in its operation. The switch generally includes an enclosed envelope with a pair of electrodes inside, with electrical leads connected to the electrodes and extending through a plastic air tube. When this envelope is positioned within the skull of the patient, the electrodes are adapted to remain closed as long as the intracranial pressure exceeds the air pressure within the envelope. In order to measure the intracranial pressure effectively, air is injected through the air tube into the envelope, the increase in air pressure tending to separate the contacting electrodes. As soon as the pressure inside the envelope balances or just exceeds the intracranial pressure, the walls of the envelope are forced apart, carrying the electrodes with them, thereby causing the electrodes to separate and break electrical contact. At this time, air flow into the envelope is terminated, and the amount of air pressure inside can then be read on a manometer or similar device. It is appreciated that the electrodes, acting as a switch, are designed to control the operation of the air flow both into and out of the envelope, and to assist in the regulation and reading of the air pressure which is inside the envelope. It is also to be appreciated that both the air and electrical connections must be made with a properly designed connector device in order to facilitate this operation. Both the operation of the Numoto-switch, and one electropneumatic junction for making this type of connection are described in U.S. Pat. No. 3,649,948.

In that patent, the electropneumatic junction provides the user with a connection device for both air and electrical lines within the same element. However, this patented electropneumatic junction is somewhat cumbersome in operation, inasmuch as the operator is required to unscrew a cap to release the sealing O-ring, and then insert the connector into the mating junction. Once that operation has been completed, the cap is then tightened to compress the O-ring in a sealing contact around the connector. For disconnection, the reverse procedure is followed. This procedure not only requires a number of hand manipulations, but also relies upon components which are intricately designed and may involve excessive expense in fabrication. Accordingly, improvements in electrofluidic, including electropneumatic, junctions are still being sought which will provide the operator with a relatively simple construction, minimal expense of manufacturer and the ability to connect and disconnect quickly with as few hand manipulations as possible.

SUMMARY OF THE INVENTION

A quick connect-disconnect electrofluidic junction assembly is utilized for simultaneously transferring fluid and electrical energy from respective sources of supply. Two general components comprise this electrofluidic junction assembly, a female terminal and a male terminal. The female terminal includes a hollow housing defining an internal receptacle, one end of which is open. A peripheral wall of the housing surrounds the receptacle. An electrical contact is positioned inside the housing, spaced apart from the open end, and has at least two electrically separated contact elements thereon in order to provide two electrical poles for use in an on/off switch. Means through the housing is provided for making an electrical lead connection to each of the two contact elements on the electrical contact. Fluid passage means extends through the housing and communicates with the receptacle, thereby providing for the flow of fluid from outside the housing into the receptacle where it will be transferred when the appropriate connection is made. The male terminal includes a hollow connector body having a cross-sectional dimension slightly smaller than the cross-sectional dimension of the receptacle so that the body may be slidably push-fit into the receptacle through its open end. On the forward end of the body is an electrical contact having at least two electrically separated contact elements adapted to mate for electrical connection purposes with the electrical contact in the housing. There is means around the periphery of the body for providing a fluid-tight seal between the body and the interior wall of the housing when inserted therein. A fluid channel extends through the body between its forward end and the peripheral sealing means, this channel communicating with the hollow interior of the body and adapted to receive fluid from the receptacle. An opening through the body communicating with its hollow interior is provided for the passage of fluid therethrough, the opening being located rearward of the peripheral sealing means. Means is provided through the body for making an electrical lead connection to each of the two contact elements on the electrical contact at the forward end of the body.

In the preferred embodiment of this aspect of the present invention, both the female receptacle and the male connector body are substantially cylindrically shaped and the sealing means is a resilient O-ring around the connector body. When the body slides into the receptacle, this O-ring provides a fluid-tight fit against the interior wall surface of the receptacle. With this feature, not only is a fluid-tight seal achieved, but the male connector fits snugly into the female receptacle merely by a push-fit connection, and a straight forward pullout for disconnection of the electrofluidic junction. No caps, screw elements, or other locking devices are required in the assembly of the present invention.

Another aspect of the present invention is the electrofluidic connector, as a separate device for utilization in junctions requiring the simultaneous transfer of electrical and fluidic energy. This connector is substantially as described above.

In accordance with the principles of the present invention, the electrofluidic junction assembly provides a quick connect-disconnect feature for situations where electrical and fluidic energy transfer are desired simultaneously. The push-fit coordination between connector and receptacle, along with appropriately placed fluid sealing elements and fluid flow passage channels, in both the receptacle and the connector, allow the operator of this assembly to complete an electrofluidic connection with one hand manipulation, with the same holding true in reverse. Moreover, the present electrofluidic junction assembly may be utilized as an in-line connection, with appropriate electrical leads and/or fluid tubes extending from each of the two general components of the assembly; or, one of the components, preferably the female terminal, may be mounted in the electrical and fluidic supply source in order to serve as a permanently attached connection medium. Thus, with the female receptacle so mounted in a supply box or casing, the male connector at the end of any device relying upon electrofluidic energy need only be plugged-in in order to make the correct connection. Other advantages are offered as well as will become more apparent when reading the detailed description of the present invention.

BRIEF DESCRIPTION OF THE DRAWINGS

FIG. 1 is a perspective view of the preferred embodiment of the quick connect-disconnect electrofluidic junction assembly;

FIG. 2 is an exploded view in perspective of the general components of the electrofluidic junction assembly of FIG. 1;

FIG. 3 is an end view looking in at the open end of the female terminal;

FIG. 4 is a partial segmented top view of the forward end of the male connector terminal;

FIG. 5 is an end view looking in at the rearward end of the male connector terminal of the assembly;

FIG. 6 is a cross-sectional view of the female terminal taken along line 6—6 of FIG. 2;

FIG. 7 is a cross-sectional view of the male terminal taken along line 7—7 of FIG. 2; and FIG. 8 is a cross-sectional view of the electrofluidic junction assembly as connected taken along line 8—8 of FIG. 1.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly to FIG. 1, there is illustrated a quick connect-disconnect electrofluidic junction assembly 10. This junction assembly is useful for applications where the simultaneous transfer of fluid and electrical energy from respective sources of supply is required. Although electrofluidic junction assembly 10 is shown in FIG. 1 as an in-line connection, it is undestood that one of the terminals of this assembly may be mounted in a casing, box or like to serve as a plug-in or plug-on connection. Electrofluidic junction assembly 10 is composed of two general components, a female terminal 12 and a male terminal 14. In general terms, male terminal 14 is adapted to fit slidably into a portion of female terminal 12 in push-fit fashion so that an electrical and fluid energy connection may be made and thus transferred through this connection. A pair of electrical leads 15 and 16 extend from female terminal 12 in order to make an electrical connection on that side of the junction, whereas another pair of electrical leads 18 and 19 extend from male terminal 14 for making the electrical connection on that side. It is noted that electrical leads 18 and 19 are enclosed inside tubing 20 which also serves as the medium through which fluid is transferred to or from the male terminal, as will be more fully described hereinafter.

Referring now to FIGS. 2, 3 and 6, the structural elements of female connector 12 are more clearly illustrated. This female terminal is comprised of a cylindrically shaped hollow housing 21 defining an internal receptacle 22, also being substantially cylindrically shaped. Inasmuch as female terminal 12 is preferably designed for mounting purposes in the monitoring-/regulating device, its nose portion 24 is tapered to facilitate such a mounting aspect; at the other end of this female terminal, a flange 25 is provided to assist in securing this terminal in its mounted position. On the other hand, if an in-line connection is made, flange 25 also serves to facilitate grasping the female terminal when the insertion of the male connector is made to complete the junction.

Receptacle 22 inside housing 21 is formed so that one of its ends is an open end 26 through which male connector 14 is adapted to be inserted. To facilitate this insertion, open end 26 has a slight chamfer 28 around its inside edge. Surrounding receptacle 22 is a peripheral wall 29, the interior surface of which is made relatively smooth so as to contribute to the fluid-tight seal which is made between that surface and the inserted male connector. Inside housing 21 and located at the internal end of receptacle 22 is an electrical contact 30. This contact is of the type which includes at least two electrically separated contact elements 31 and 32 so that a two pole electrical connection can be made to this female terminal. In the embodiment being described, electrical contact 30 is preferably a female type with a central opening 34 extending therethrough for reception of a mating electrical contact. Appropriate threads 35 are tapped into housing 21 so that electrical contact 30 may be screwed into this part of the housing for final securement. A bore 36 is provided in the nose end of the female connector so that electrical contact elements 31 and 32 may extend freely therein. At the tip 37 of nose end 24, two holes 38 and 39 are formed, with hole 39 communicating with bore 36. Hole 39 is used for making an electrical lead connection to each of the two contact elements 31 and 32 on the electrical contact. A passageway 40 is formed through housing 21 so that it extends from the internal wall of receptacle 22 through the housing and communicates with hole 38 at the nose tip. This passageway permits fluid to flow from an outside environment through the housing and then into receptacle 22 whereby the fluid may be then transferred from the female terminal to the male terminal for the particular use for which it is being employed, such as in an intracranial monitoring device. Passageway 40 need only be a small diameter hole communicating with receptacle 22 inasmuch as the fluid, such as air, flow requirements are generally not large for this type of device. In fabricating this female terminal, the short leg 37 between hole 38 and passageway 40 can be drilled, and then smoothly plugged on the outside so that air is directed only along the paths of the hole, leg and passageway.

In FIGS. 2, 4, 5 and 7, the elements of male terminal 14 are illustrated in greater detail. This male terminal includes a substantially cylindrically shaped connector body 42. The cross-sectional dimension of body 42, particularly its outside diameter, is slightly smaller than the cross-sectional dimension of receptacle 22 inside the female terminal. This, of course, will permit connector body 42 to fit slidably into the receptacle of the female terminal through its open end. Connector body 42 is also hollow with an interior passage 44 extending completely therethrough. An electrical contact 45 is positioned on the forward end 46 of the connector body, and is maintained in position by being screwed into the threaded portion 48 of the forward end 46 of the connector body. Electrical contact 45 is selected to mate with electrical contact 30 in the female terminal of this electrofluidic junction assembly. Accordingly, electrical contact 45, in this embodiment, is a male contact, having a contact post 49 protruding substantially axially away from forward end 46 of the connector body. Two electrically separated contact elements 50 and 51 are provided on this electrical contact so that two electrical leads may be connected thereto in order to serve as a two pole device such as for switching purposes. Electrical contact elements 50 and 51 extend into hollow passage 44 so that the connection by the electrical leads to these contacts will be hidden.

Spaced a short distance from the forward end of the connector body is a resilient O-ring 52, preferably made from a soft, elastomeric material. This O-ring is held in place around the connector body by being mounted in a suitable groove 54 formed in the periphery of the body. The depth of groove 54 and the thickness of O-ring 52 is such that the outside diameter of the O-ring is slightly larger than the diameter of connector body 42, and is also slightly larger than the interior diameter of the peripheral wall 29 surrounding receptacle 22 in the female terminal. These dimensional characteristics accordingly provide an interference fit between the O-ring and the receptacle wall of the female terminal. Between forward end 46 of the connector body and O-ring 52, a fluid channel 55 is formed. This channel 55 terminates in a hole 56 through the wall of a connector body 42 and communicates with hollow passage 44 inside the connector body. Channel 55 and hole 56 are thus adapted to receive fluid from the receptacle of the female terminal after the male connector is inserted therein. Once the fluid flows through the fluid channel and hole into the interior passage of the connector body, it travels toward the rearward end 58 of the connector body. In this rearward end, a hollow pin 59 is mounted, with its lumen 60 thereby serving as an opening through which the fluid may exit after passing through the connector body. Inasmuch as lumen 60 communicates with interior passage 44, it also serves as the medium through which the electrical leads extending from the electrical contact may pass in order to make an electrical connection, as described hereinafter. In addition, this pin is adapted to receive an open end of tubing so that the fluid which passes from the connector body can be appropriately controlled. While pin 59 is illustrated at the end surface of the rearward end of the connector body, such a pin or opening may be provided through the connector body at any desirable point rearward of the O-ring as may be convenient for the specific application in which this device is being used.

Turning to FIG. 8, electrofluidic junction assembly 10 is illustrated with its general components, female terminal 12 and male terminal 14 connected in the appropriate position to provide for the simultaneous transfer of both fluid and electrical energy therethrough. As seen in this Figure, connector body 42 has been inserted into receptacle 22 of the female terminal. The resiliency of O-ring 52 permits the same to be compressed radially inwardly in order to provide a fluid-tight fit with the compressing surface, namely peripheral wall 29 surrounding receptacle 22. Male electrical contact 45 on the connector body is in direct contact with female electrical contact 30 inside the female terminal, electrical contact 30 serving as an abutment stop for the forward end of the connector body. Electrical contact thus being made, electrical energy is thus transferred by electrical leads 15 and 16 through the female terminal and continued by electrical leads 18 and 19 through the male terminal. Electrical leads 15 and 16 are potted into hole 39 with a suitable potting compound; electrical contacts 30 and 45 are sealed with a suitable anti-rotation material, so that the electrical connections are fluid-tight and will not leak. This electrical contact position is readily accomplished merely by the single-step insertion of male connector into the female receptacle until the forward end of the connector is properly seated. It is appreciated that when the female terminal is mounted in a supply box in the regulating system, insertion of the connector body is merely a plug-in type connection.

Fluid, such as air, may be channeled through hole 38 in the female terminal and then through passage 40 so that the fluid may enter the receptacle 22. Inasmuch as O-ring 52 effectively provides a fluid-tight seal, the fluid, normally under pressure, is thereby directed into fluid channel 55 and hole 56 in the interior passage of the connector body. Fluid flow then passes through hollow pin 59 into the interior of tubing 20 which is connected to pin 59. It is noted when viewing FIG. 8, that electrical leads 18 and 19 in the male connector also extend through hollow pin 59, there being sufficient room in the lumen of the pin to handle both fluid flow and the electrical leads. It is appreciated that, although the direction of fluid flow has been described as passing from the female terminal to the male terminal, fluid flow may also travel in the reverse direction with the same desirable results. When the electrofluidic operation has been completed, the operator merely has to unplug the male connector by pulling the same directly out of the female terminal. No unscrewing or unlocking steps are required as in other junctions which are employed in simultaneous electrofluidic energy transfer.

While many materials may be used to fabricate the components of the present invention, rigid plastic materials are preferred due to their durability, light-weight properties, ease of fabrication, and the fact that they are electrically non-conductive so that further electrical insulation is not necessary when mounting the electral contacts therein. The electrical contacts which are employed in this invention may be selected from many standard mating connectors of the male-female type, and especially which provide at least two electrical contacts for providing a two pole connection. The hollow pin on the male connector is also selected from a variety of pins of the standard type which have a hollow opening therethrough and which will accommodate a tubing around its outside periphery. In fabricating the components of the present invention, standard molding processes may be utilized in order to minimize expense of these components. In order to assist the operator's grasp when connecting and disconnecting the male connector, the connector body may include a knurled surface in the rearward portion. While the size of the components of the present invention may be devised according to its intended use, a typical assembly may have both male and female terminals in the order of two inches (5.1 centimeters) in length, with the diameter of the male connector body being about ½ inch (1.25 centimeters).

Thus, the present invention provides a quick connect-disconnect electrofluidic junction assembly which may be utilized in a variety of applications involving the simultaneous transfer of electrical and fluid energy, and particularly in monitoring systems such as the measurement of intracranial pressure and the like.

I claim:

1. A quick connect-disconnect electrofluidic junction assembly for simultaneously transferring fluid and electrical energy from respective sources of supply comprising a female terminal and a male terminal, said female terminal including: a hollow housing defining an internal receptacle, one end of said receptacle being open, said receptacle being defined by a peripheral wall on the housing surrounding said receptacle; an electrical contact having at least two electrically separated contact elements thereon, said contact positioned inside said housing and spaced apart from said open end; means through said housing for making an electrical lead connection to each of said two contact elements on said contact; and fluid passage means through said housing and communicating with said receptacle; and said male terminal including: a hollow connector body having a cross-sectional dimension slightly smaller than the cross-sectional dimension of said receptacle so that said body may slidably fit into said receptacle through the open end thereof; an electrical contact having at least two electrically separated contact elements positioned on the forward end of said body adapted to mate for electrical connection purposes with said electrical contact in said housing; means around the periphery of said body for providing a fluid-tight seal between said body and the interior wall of said housing when slide-fit therein; a fluid channel through said body between its forward end and said peripheral sealing means, said channel communicating with the hollow interior of said body and adapted to receive fluid from said receptacle; an opening through said body communicating with said hollow interior of said body for the passage of fluid therethrough, said opening being located rearward of said peripheral sealing means; and means through said body for making an electrical lead connection to each of said two contact elements on said contact at the forward end of said body.

2. The electrofluidic junction assembly of claim 1 wherein said receptacle is substantially cylindrically shaped and the interior surface of said surrounding wall is relatively smooth, and wherein said connector body is substantially cylindrically shaped and said sealing means is a resilient O-ring having an outside diameter slightly larger than the diameter of said body and adapted to slide with said body into said receptacle to provide a fluid-tight fit against said smooth wall surface.

3. The electrofluidic junction assembly of claim 1 wherein the electrical contact inside said housing is a female contact into which the electrical contact of said body is mated, said female contact serving as an abutment stop for the forward end of said body when inserted into said receptacle.

4. The electrofluidic junction assembly of claim 3 wherein the electrical contact on the forward end of said body is a male contact protruding substantially axially from said forward end.

5. The electrofluidic junction assembly of claim 1 wherein said opening for said fluid passage communicates with the lumen of a hollow pin connected to the rearward end of said body, said pin adapted to receive electrical leads through its lumen so that both electrical and fluid energy pass through said pin.

6. An electrofluidic connector for use in providing a junction to simultaneously transfer fluid and electrical energy from respective sources of supply comprising: a hollow body; an electrical contact having at least two electrically separated contact elements connected to a forward end of said body for making an electrical connection to a mating electrical contact during use; means around the periphery of said body adapted to provide a fluid-tight seal between said body and a wall surface of a mating receptacle into which said body may be slidably fit; a fluid channel through said body between its forward end and said peripheral sealing means, said channel communicating with the hollow interior of said body and adapted to pass fluid therethrough into said hollow interior; an opening for the passage of fluid communicating with said hollow interior of said body and located rearward of said peripheral sealing means; and means through said body for making an electrical lead connection to each of said two contact elements on said contact at the forward end of said body.

7. The electrofluidic connector of claim 6 wherein said body is substantially cylindrically shaped and said sealing means is a resilient O-ring having an outside diameter slightly larger than the diameter of said body and adapted to compress radially inwardly to provide a fluid-tight fit with a compressing surface.

8. The electrofluidic connector of claim 6 wherein said electrical contact is a male contact protruding substantially axially from said forward end.

9. The electrofluidic connector of claim 6 wherein said opening serves as the means for making said electrical lead connection to said electrical contact in addition to serving as a fluid passage medium.

10. The electrofluidic connector as defined in claim 9 wherein said opening is through the rearward end of said body and it communicates with the lumen of a hollow pin connected to said rearward end, said pin adapted to receive electrical leads through its lumen and to receive an open end of tubing for transfer of fluid therethrough so that both electrical and fluid energy pass through said pin.

* * * * *